United States Patent [19]
Sirhan et al.

[11] Patent Number: 5,279,562
[45] Date of Patent: Jan. 18, 1994

[54] LOW PROFILE PERFUSION-TYPE DILATATION CATHETER

[75] Inventors: Motasim M. Sirhan, Sunnyvale; Andrew Lerohl, San Jose; Jovito L. Fernando, Modesto, all of Calif.

[73] Assignee: Advanced Cardiovascular Systems, Inc., Santa Clara, Calif.

[21] Appl. No.: 6,178

[22] Filed: Jan. 15, 1993

Related U.S. Application Data

[63] Continuation of Ser. No. 734,892, Jul. 24, 1991, abandoned.

[51] Int. Cl.⁵ .............................. A61M 25/00
[52] U.S. Cl. ......................... 604/96; 606/194
[58] Field of Search ............ 604/280, 281, 93–96, 604/101; 606/191–194

[56] References Cited

U.S. PATENT DOCUMENTS

| | | | |
|---|---|---|---|
| 3,915,171 | 10/1975 | Shermeta | 604/101 |
| 4,737,153 | 4/1988 | Shimamura et al. | 604/282 |
| 4,748,982 | 6/1988 | Horzewski et al. | 604/102 |
| 4,892,519 | 1/1990 | Songer et al. | 604/96 |
| 4,925,445 | 5/1990 | Sakamoto et al. | 604/281 |
| 4,944,745 | 7/1990 | Sogard et al. | 604/194 |
| 4,990,143 | 2/1991 | Sheridan | 604/282 |

Primary Examiner—C. Fred Rosenbaum
Assistant Examiner—Manuel Mendez
Attorney, Agent, or Firm—Crosby, Heafey, Roach & May

[57] ABSTRACT

A balloon dilatation catheter which has a coiled supporting element disposed within a guidewire receiving inner lumen extending within the interior of the balloon. Substantially lower profiles can be obtained with catheters of this type, particularly with perfusion-type dilatation catheters with little chance that the inner member will collapse when the balloon is inflated to high pressures. Additionally, the coiled supporting element provides much smoother transitions at the ends of the balloon and thereby improves the trackability of the catheter over a guidewire.

9 Claims, 2 Drawing Sheets

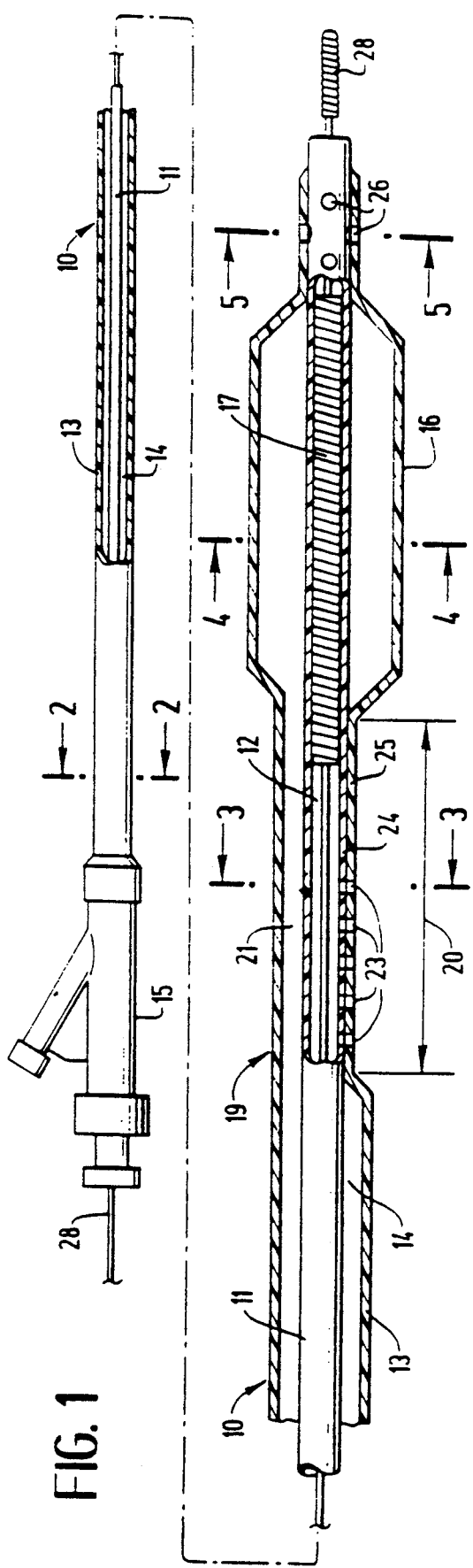

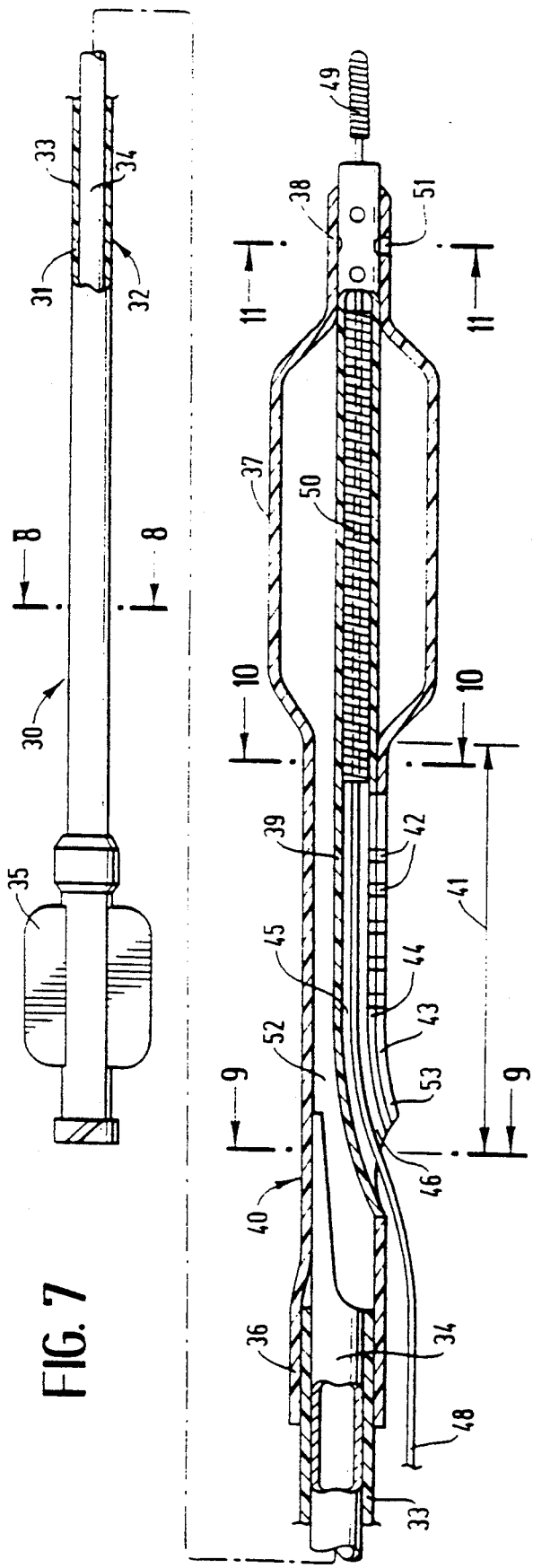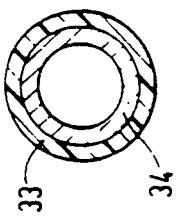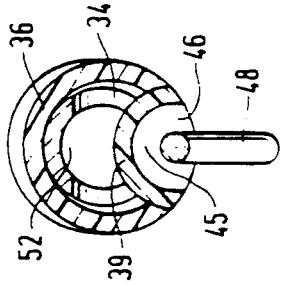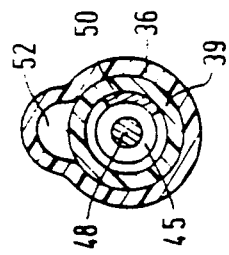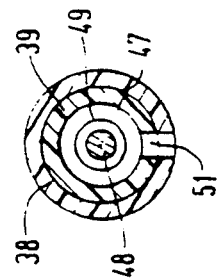

LOW PROFILE PERFUSION-TYPE DILATATION CATHETER

This is a continuation of copending application Ser. No. 07/734,892 which was filed on Jul. 24, 1991, now abandoned.

BACKGROUND OF THE INVENTION

This invention generally relates to intravascular catheters, such as balloon dilatation catheters used in percutaneous transluminal coronary angioplasty (PTCA).

In classic PTCA procedures, a guiding catheter having a preshaped distal tip is percutaneously introduced into the cardiovascular system of a patient and advanced therein until the preshaped distal tip of the guiding catheter is disposed within the aorta adjacent to the ostium of the desired coronary artery. The guiding catheter is twisted or torqued from the proximal end to turn the distal tip of the guiding catheter so that it can be guided into the coronary ostium. A guidewire and a balloon dilatation catheter are introduced into and advanced through the guiding catheter to the distal tip thereof, with the guidewire slidably disposed within an inner lumen of the dilatation catheter. The guidewire is first advanced out the distal tip of the guiding catheter, which is seated in the ostium of the patient's coronary artery, until the distal end of the guidewire crosses the lesion to be dilated. The dilatation catheter is then advanced out of the distal tip of the guiding catheter, over the previously advanced guidewire, until the balloon on the distal extremity of the dilatation catheter is properly positioned across the lesion. Once properly positioned, the balloon is inflated to a predetermined size with radiopaque liquid at relatively high pressures (e.g., generally 4-12 atmospheres) to dilate the stenosed region of the diseased artery. The balloon is then deflated so that the dilatation catheter can be removed from the dilated stenosis and blood flow will resume therethrough.

Further details of guiding catheters, dilatation catheters, guidewires, and other devices for angioplasty procedures can be found in U.S. Pat. No. 4,323,071 (Simpson-Robert); U.S. Pat. No. 4,439,185 (Lundquist); U.S. Pat. No. 4,468,224 (Enzmann et al.); U.S. Pat. No. 4,516,972 (Samson); U.S. Pat. No. 4,438,622 (Samson) et al.); U.S. Pat. No. 4,554,929 (Samson et al.); U.S. Pat. No. 4,582,185 (Samson); U.S. Pat. No. 4,616,652 (Simpson); U.S. Pat. No. 4,638,805 (Powell); U.S. Pat. No. 4,748,986 (Morrison et al.); U.S. Pat. No. 4,898,577 (Badger et al.); and U.S. Pat. No. 4,827,943 (Taylor et al.) which are hereby incorporated herein in their entirety by reference thereto.

Several notable improvements have recently been made in balloon angioplasty catheters. One such modification is described in U.S. Pat. No. 4,748,982 (Horzewski et al.) wherein a short sleeve or inner lumen at least about 10 cm in length is provided within the distal section of t he catheter body which extends from a first port proximal to the balloon to a second port in the distal end of the catheter and which is adapted to slidably receive a guidewire. The proximal port is not less than about 10 cm and not more than about 40 cm from the distal end of the catheter. Preferably, a slit is provided in the catheter body extending from the proximal port to a location proximal to the proximal end of the balloon to facilitate the removal of the catheter from the proximal end of the guidewire which extends out of the patient.

Another modification, which was introduced into the market place by the assignee of the present application (Advanced Cardiovascular Systems, Inc.), has been perfusion-type dilatation catheters which allow for long term dilatations to repair arterial dissections and other arterial damage. These perfusion catheters have a plurality of perfusion ports in the wall forming at least part of the catheter body proximal to the balloon which are in fluid communication with an inner lumen extending to the distal end of the catheter body. A plurality of perfusion ports are preferably provided in the catheter body distal to the balloon which are also in fluid communication with the inner lumen extending to the distal end of the catheter body. When the balloon on the distal extremity of the dilatation catheter is inflated to dilate a stenosis, oxygenated blood in the artery or the aorta or both, depending upon the location of the dilatation catheter within the coronary anatomy, is forced to pass through the proximal perfusion ports, through the inner lumen of the catheter body and out the distal perfusion ports. This provides oxygenated blood downstream from the inflated balloon to thereby prevent or minimize ischemic conditions in tissue distal to the catheter to thereby facilitate long term dilatations. As is appreciated by those skilled in the art, tissue distal to a stenosis is frequently already in jeopardy due to ischemic conditions which may exist. As a result, care should be exercised in sizing the perfusion ports and the inner lumen to ensure that there is adequate flow of oxygenated blood to tissue distal to the catheter to eliminate or minimize ischemic conditions. Unfortunately, commercially available perfusion catheters have relatively large profiles due to the size of the inner tubular member which extends through the interior of the balloon which prevents their use in many distal coronary locations.

A major and continual thrust of development work in the field of intravascular catheters, particularly coronary angioplasty catheters, has been to reduce the profile, i.e. transverse dimensions, of such catheters and to improve the flexibility thereof without detrimentally affecting the pushability, particularly in the distal portion of such catheters. A reduction in profile with little or no loss in pushability allows a dilatation catheter to be advanced much further into a patient's coronary vasculature and to cross much tighter lesions.

Despite many advances in this field, a need remains for lower profile, perfusion type dilatation catheters having greater flexibility with little or no loss in pushability. The present invention satisfies this need.

SUMMARY OF THE INVENTION

This invention is directed to an improved balloon angioplasty catheter which is adapted to perfuse blood distal to the catheter when the balloon thereon is inflated during an agioplasty procedure.

The intravascular catheter of the invention includes an elongated catheter shaft having at least one inner lumen extending therein, an inflatable member on the distal extremity of the catheter shaft having an interior in fluid communication with the inner lumen in the catheter shaft and a tubular element, preferably a thin walled tubular element, extending through the interior of the balloon which is adapted to perfuse blood from a location proximal to the inflatable member to a location distal to the inflatable member. A support means, such as a coiled spring, is disposed within an inner lumen extending through the thin walled tubular element to provide support thereto and to prevent the collapse thereof upon the inflation of the inflatable member.

In a presently preferred embodiment, the supporting member for the thin walled tubular element extended beyond at least one end, and preferably both ends, of the inflatable member to facilitate a smooth transition between the inflatable member and adjacent sections of the catheter and thereby improve the trackability of the catheter over a guidewire. A suitable support member is a helical coil formed of flat ribbon of high strength metal such as stainless steel, e.g. 304 alloy, and Nitinol, particularly with superelastic properties. The transverse dimensions of the ribbon are about 0.0005 to about 0.002 inch (0.013–0.051 mm) in thickness and about 0.003 to about 0.01 inch (0.076–0.254 mm) in width. Although it is preferred to have the individual turns of the coil stacked against one another, the coil may be extended up to 50% of its length when the turns are stacked against one another.

The improved catheter construction of the invention is particularly suitable for use in dilatation catheters described in copending application Ser. No. 07/700,617 filed May 15, 1991 (Sirhan et al.) entitled "Low Profile Dilatation Catheter" and which is incorporated herein in its entirety by reference.

The catheter shaft of the dilatation catheter described in the Sirhan et al. application has a distal section with an inner tubular member having an inner lumen extending therein and an outer tubular member disposed about the inner tubular member. In the distal section, a length of the outer tubular member is bonded by a substantial part of the inner surface or inner periphery thereof to the outer surface of the inner tubular member. At least about 15% to about 90%, preferably about 40% to about 80%, of the periphery of the outer tubular member is bonded to the underlying inner tubular member so that the bonded portion of the outer member takes the shape of the inner tubular member to which it is bonded. The unbonded portion of the outer tubular member along said length defines with the inner tubular member a longitudinally extending inner lumen.

The bond between the inner and outer tubular members need not be continuous, i.e. may be intermittent, so long as a significant portion thereof is bonded. The bonded section may extend along essentially the entire length of the catheter but should not be less than about 1 cm. Preferably, the length of the bonded section is about 10 cm to about 40 cm. By bonding a length of the outer tubular member in the distal portion of the catheter to the exterior of the inner member, the profile of the catheter body in at least one transverse dimension in that area is reduced substantially to thereby provide improved flexibility. Moreover, the bonded portions of the inner member and the outer tubular members support one another thereby providing an improvement in the pushability of the catheter. Substantial reductions in only one transverse dimensions can provide substantial improvements is flexibility. Minimum cross-sectional dimensions of the distal section of the catheter body for coronary dilatation catheters are on the order of about 0.02 to about 0.06 inch (0.51–1.5 mm). For peripheral arteries this dimension may be larger.

The coil supported, thin walled inner tubular member which is adapted to perfuse blood through the interior of the balloon has little tendency to collapse upon the inflation of the balloon, even to inflation pressures of 350 psi or more. Additionally, the coil support provides much smoother transitions which result in improved trackability of the catheter over a guidewire. These and other advantages of the invention will become more apparent from the following detailed description of the invention when taken in conjunction with the accompanying exemplary drawings.

BRIEF DESCRIPTION OF THE DRAWINGS

FIG. 1 is an elevational view, partially in section, of a perfusion-type balloon dilatation catheter embodying features of the invention.

FIG. 2 is a transverse cross-sectional view of the catheter shown in FIG. 1 taken along the lines 2—2.

FIG. 3 is a transverse cross-sectional view of the catheter shown in FIG. 1 taken along the lines 3—3.

FIG. 4 is a transverse cross-sectional view of the catheter shown in FIG. 1 taken along the lines 4—4.

FIG. 5 is a transverse cross-sectional view of the catheter shown in FIG. 1 taken along the lines 5—5.

FIG. 6 is a transverse cross-sectional view of the ribbon forming the helical oil disposed within the inner tubular member shown in FIGS. 1-5.

FIG. 7 is an elevational view, partially in section, of another perfusion-type balloon dilatation catheter embodying features of the invention.

FIG. 8 is a transverse cross-sectional view of the catheter shown in FIG. 7 taken along the lines 8—8.

FIG. 9 is a transverse cross-sectional view of the catheter shown in FIG. 7 taken along the lines 9—9.

FIG. 10 is a transverse cross-sectional view of the catheter shown in FIG. 7 taken along the lines 10—10.

FIG. 11 is a transverse cross-sectional view of the catheter shown in FIG. 7 taken along the lines 11—11.

DETAILED DESCRIPTION OF THE INVENTION

FIGS. 1-5 schematically illustrate an over-the-wire, perfusion type dilatation catheter embodying features of the invention. The catheter includes an elongated catheter body 10 which has an inner tubular member 11 with an inner lumen 12, an outer tubular member 13 disposed about the inner tubular member and defining therebetween an annular inner lumen 14 which extends through the proximal portion of the catheter body. An adapter 15 is secured to the proximal ends of the inner and outer tubular members 11 and 13. A relatively inelastic, inflatable balloon 16 is formed as part of the outer tubular member 13 with the distal end of the balloon secured to the distal end of the inner tubular member 11. The balloon 16 may be formed from the sam tubing as the outer tubular member 13 as shown in FIG. 1 or it may be made separately from the same or different materials and secured to the distal end of the outer tubular member as is well known to those skilled in the art.

A helical coil 17 formed of flat ribbon 18 is disposed within the inner tubular member 11 and extends therein between the ends of the balloon 16. A transverse cross section of the ribbon 18 is shown in FIG. 6 illustrating the rectangular shape thereof. Typically, the cross-sectional dimensions of the ribbon 18 are about 0.0015 inch (0.038 mm) thick and about 0.01 inch (0.25 mm) in width, although other dimensions may be employed depending upon the strength of the material from which the coil 17 is made and upon the needs of the particular balloon dilatation procedure. While the individual turns of the coil 17 are preferably stacked adjacent to one another, the coil may be stretched to provide space between the individual turns of the coil.

The outer tubular member 13 generally has a distal section 19 with small transverse dimensions in at least one direction. As best shown in FIGS. 1 and 3, a length 20 of the distal section 19 is bonded to the exterior of the inner tubular member 11 with a significant portion of the periphery outer member 13, typically about 50% to about 80%, being bonded to the inner tubular member. The unbonded portion 21 of the distal section 19 along the length 20 forms an inflation lumen 21 which is in fluid communication with the interior of the balloon 16 and the annular lumen 14. A plurality of perfusion ports 23 proximal to the balloon 16 which pass through the bonded walls 24 and 25 of the inner and outer tubular members 11 and 13, respectively, and which are in fluid communication with the inner lumen 12 of the inner tubular member 11. Additionally, one or more perfusion ports 26 are provided distal to the balloon through the wall 27 of the inner tubular member 11 and are in fluid communication with the inner lumen 12 extending therein. In this manner, when the balloon 16 is inflated during an angioplasty procedure within a patient's vasculature, oxygenated blood is forced to pass through the proximal perfusion ports 23, through the inner lumen 12 and then out the distal perfusion ports 26 to provide oxygenated blood distal to the catheter and thereby avoid the generation of ischemic conditions in tissue downstream thereof. The transverse dimensions of the inner lumen 12 of the tubular member 11 within the bonded section should be large enough to allow for an adequate flow of blood therethrough when the guidewire 28 is withdrawn sufficiently from the perfusion portion of the inner lumen 12 to avoid impeding blood flow.

The use of the dilatation catheter shown in FIGS. 1-6 generally follows conventional PTCA practices with over-the-wire perfusion-type dilatation catheters. A guidewire 28 is backloaded into the inner lumen 12 of the inner tubular member 11 of the catheter body 10 and both the guidewire and the catheter are advanced together through a guiding catheter (not shown) which has been previously disposed within the patient's arterial system, with the distal end of the guiding catheter seated within the ostium of the desired coronary artery. The guidewire 28 is advanced out the distal end of the guiding catheter into the patient's coronary anatomy until it crosses the lesion to be dilated, and then the dilatation catheter is advanced over the guidewire which is being held in its position, until the balloon 16 on the dilatation catheter is properly disposed within the stenotic region. The lesion is dilated by directing inflation fluid through the annular lumen 14 and the inflation lumen 22 formed by the unbonded portion of the outer tubular member 13 to inflate the balloon 16. The balloon 16 can be maintained in the inflated condition for long periods, e.g. typically about 20-30 minutes but in some instances up to 5 hours or more. Upon inflation, the balloon 16 occludes the arterial lumen causing oxygenated blood within the coronary artery to flow through the proximal perfusion ports 23 into the inner lumen 12 and out the distal perfusion ports 26 to tissue distal to the inflated balloon so as to prevent or minimize the severity of ischemic conditions at the distal location. Preferably, the guidewire 28 is pulled back into the inner lumen 12 of the catheter to a location therein so that the distal end of the guidewire is proximal to the proximal perfusion ports 23 to avoid interference with the flow of blood through the inner lumen 12. After the dilatation, the balloon 16 is deflated and the catheter and the guidewire 28 may then be withdrawn from the patient. If further treatment or diagnosis to be conducted, the guidewire can be replaced with an exchange wire before removing the dilatation catheter so that the first catheter can be removed and another advanced into the desired location or an extension wire can be attached to the proximal end of the guidewire in place to perform essentially the same function. See the discussion of exchange wires and extension wires in U.S. Pat. No. 4,827,941 (Taylor et al.) which has been incorporated herein by reference.

FIGS. 7-11 schematically illustrate another embodiment of the perfusion dilatation catheter of the invention. In this embodiment the catheter includes a body 30 having an outer tubular member 31 with a two layered proximal portion 32 which has an outer plastic tubular coating or jacket 33 which fits tightly, e.g. is shrunk fit, onto an inner tubular element 34 which is preferably formed of hypotubing, An adapter 35 is secured to the proximal end of the catheter body 30. The proximal skirt 36 of the relatively inelastic balloon 37 is secured to the distal end of the outer plastic element 33. The distal skirt 38 of the balloon 37 is bonded to the distal end of the inner tubular member 39. The catheter body 30 has a flexible distal section 40 where a significant portion of the interior surface of the proximal skirt 36 of the balloon 37 along a length 41 is bonded to the exterior of the inner tubular member 39. A plurality of perfusion ports 42 extend through the bonded walls 43 and 44 of the balloon skirt 36 and the inner tubular member 39, respectively and are in fluid communication with inner lumen 45 of the inner tubular member 39. To this extent, the distal end of this embodiment is quite similar to the embodiment shown in FIGS. 1-6.

In the embodiment shown in FIGS. 7-11, the catheter body 30 is provided a proximal guidewire port 46 which passes through the bonded walls 43 and 44 of the balloon skirt 36 and the inner tubular member 39 respectively and which is in fluid communication with a relatively short inner lumen 45 extending within the distal portion of the inner tubular member 39. A distal guidewire port 47 is provided at the distal end of the inner tubular member 39 in communication with the inner lumen 45 thereof. Guidewire 48 extends proximally through the inner lumen 45 and out the proximal port 46 and the coil 49 on the distal end of the guidewire 48 extends out the distal port 47 in the distal end of the inner tubular member 39. A supporting helical coil 50 is disposed within the inner lumen 45 of the tubular member 39 and extends between the proximal and distal ends of the balloon 37 and preferably between the proximal perfusion ports 42 and the distal perfusion ports 51.

The inner tubular element 34 onto which the outer plastic jacket 33 is secured is preferably hypotubing and may be formed of stainless steel, such as 304 alloy, or of a NiTi alloy, particularly a NiTi alloy with superelastic properties, such as described in co-pending application Ser. No. 07/692,381, filed Dec. 18, 1990; entitled "Superelastic Guiding Member" and assigned to the present assignee, Advanced Cardiovascular Systems, Inc. The distal extremity of the inner tubular element 34 is truncated to fit will into the inner lumen 52 in the proximal portion of the proximal skirt 36 of the balloon 37 which is not bonded to the inner tubular member 39 to direct inflation fluid to the interior of the balloon.

The catheter construction of this embodiment with a relatively short inner lumen which is adapted to slidably receive a guidewire therein eliminates the need for using an exchange wire or a guidewire extension. A slit 53 is preferably provided in the bonded walls 43 and 44 of the inner tubular member 39 and the proximal skirt 36 extending from the proximal guidewire port 46 to a location adjacent the proximal end of the balloon 37, preferably through the proximal perfusion ports 42. The slit 53 greatly facilitates the removal of the catheter from the proximal end of the guidewire 48 when the catheter is to be replaced or exchanged for another catheter and it also eliminates the need for using a guidewire extension or an exchange wire as described in Horzewski et al., which has been incorporated herein by reference.

There are at least two modes of inserting the dilatation catheter of this embodiment into the patient's coronary anatomy. The first method is for the most part the same as in the prior embodiment, namely, the guidewire 48 is preloaded into the short inner lumen 45 of the inner tubular member 39 of the catheter body 30 and both are advanced through a guiding catheter (not shown) previously disposed within the patient's arterial system with the distal end of the guiding catheter seated within the ostium of the desired coronary artery. The second mode, frequently called the "bare wire" technique, involves fire advancing a guidewire 48 through and out the guiding catheter until it is positioned within the patient's coronary artery across the lesion to be dilated. The proximal end of the guidewire 48, which is outside the patient, is backloaded, i.e. inserted into the short inner lumen 45 of the inner tubular member 39 and advanced proximally therein until it exits the proximal guidewire port 46. The proximal end of the guidewire 48 is held in place and the catheter is advanced over the guidewire through the patient's vascular system until the dilatation balloon 37 on the catheter is positioned across the stenotic region so that the stenosis can be dilated upon the inflation of the balloon. The inflated balloon 37 occludes the arterial passageway causing blood to flow through the proximal perfusion ports 42 into the inner lumen 45 and out the distal perfusion ports 51 to minimize ischemic conditions in tissue distal to the balloon. As in the previously discussed embodiment, the balloon can be maintained in the inflated condition for extended periods. After the dilatation of the lesion, the balloon 37 is deflated and the catheter may be removed from the patient's artery. If other treatments are necessary, the catheter is slidably removed over the guidewire 48, leaving the guidewire in place so that other catheters can be advanced over the in-place guidewire in a similar manner without the need for exchange wires or guidewire extensions.

The above described perfusion-type catheters may be made by conventional techniques well known to those skilled in the art, and many of these suitable techniques are described in the references incorporated herein. The bonded distal sections 19 and 40 may be formed by heat shrinking the portion of the outer tubular members 13 and proximal skirt 36 which form the distal sections onto the underlying inner members 11 and 39. A mandrel (not shown) is disposed in the space between the inner and outer tubular members 11 and 13 and the skirt 36 and the inner tubular member 39 so that upon the heat shrinking of the outer tubular member or skirt an inflation lumen is formed through the distal sections which is in fluid communication with the lumen in the proximal portion of the catheter body and the interior of the balloon. Another mandrel may be inserted into the inner lumen of the inner tubular member to support and shape the latter during the heat shrinking of the outer tubular member thereon. Alternate methods may be employed to make the distal section. For example, the distal sections 19 and 40 may be preformed and then be adhesively bonded to the exterior of the inner tubular member. Multiple lumens similar to the inflation lumen may be formed in the distal sections, such as the top and bottom thereof, by employing multiple mandrels when heat shrinking the outer tubular member onto the exterior of the inner tubular member.

The various components of the catheters and guidewires of the invention can be formed from a wide variety of conventional materials. The inner and outer plastic tubular members may be made from polyethylene, polyesters, polyimide, polyvinyl chloride and other suitable plastic materials. The hypotubing may be formed of stainless steel, NiTi superelastic alloys or other suitable materials. Composite materials such as described in co-pending application Ser. No. 07/241,047, filed Sep. 6, 1988 (which is incorporated herein by reference thereto) may also be used. The balloon may be made from polyethylene, polyethylene terephthalate and other suitable polymers and other materials.

The dimensions of the catheters generally follow the dimensions of conventional intravascular catheters. For coronary use the length is typically about 135 cm and the outer diameter of the outer tubular member is about 0.02 to about 0.06 inch. The inner tubular member into which the coil or other support is disposed generally has an inner lumen with a diameter of about 0.015 to about 0.035 inch (0.38–0.89 mm) and a wall thickness of up to about 0.0015 inch (0.38 mm) and preferably about 0.0008 to about 0.0012 inch (0.02–0.03 mm). In a presently preferred embodiment, the flexible distal section is long enough (e.g. the proximal end of the distal section is preferably about 15 to about 40 cm from the distal end of the catheter) to ensure that the distal section is the only portion of the catheter body proximal to the balloon which exits the guiding catheter and enters the patient's coronary anatomy during intravascular procedures. The transverse dimensions of the catheter may be larger for catheters used in peripheral arteries and other locations.

Those skilled in the art will recognize that modifications and improvements can be made to the invention without departing from the scope thereof.

What is claimed is:

1. A balloon dilatation catheter adapted to be advanced within a patient's arterial system and to perfuse blood to an arterial location distal to the catheter upon the inflation of a balloon thereon comprising:
    a) an elongated catheter body having proximal and distal ends and an inner inflation lumen extending from the proximal end to the distal end thereof;
    b) a multilumen distal section at the distal end of the elongated catheter body having a portion of the inner inflation lumen of the elongated catheter body and a second inner lumen extending between at least one distal perfusion port in a distal portion of the multilumen distal section and at least one proximal perfusion port in a proximal portion of the multilumen distal section, said second inner lumen being defined by a tubular member;
    c) an inflatable dilatation balloon having proximal and distal ends secured to the multilumen distal section at locations between the proximal and distal perfusion ports, and having an interior which is in fluid communication with the portion of the inner inflation lumen in the distal section; and d) a tubular shaped helical coil supporting element which is disposed within the second inner lumen, extending through the tubular member from a location distal to the proximal perfusion ports and proximal to the inflatable dilatation balloon to a location distally beyond at least the proximal end of the inflatable balloon.

2. The balloon dilatation catheter of claim 1 wherein the coiled supporting element disposed within the second inner lumen is formed from ribbon.

3. The balloon dilatation catheter of claim 2 wherein the ribbon is formed of material selected from the group consisting of stainless steel and NiTi alloys having superelastic properties.

4. The balloon dilatation catheter of claim 1 wherein the second inner lumen is adapted to receive a guidewire and extends between a first guidewire port in a proximal portion of the multilumen distal section and a second guidewire port in a distal portion of the multilumen distal section.

5. The balloon dilatation catheter of claim 1 wherein the coiled supporting element extends beyond both ends of the inflatable dilatation balloon.

6. The balloon dilatation catheter of claim 1 wherein the coiled supporting element fits tightly within the second inner lumen.

7. The balloon dilatation catheter of claim 6 wherein the multilumen distal element is heat shrunk so that the coiled supporting element fits tightly within the second inner lumen thereof.

8. The balloon dilatation catheter of claim 1 wherein the multilumen distal section has a guidewire receiving port located proximal to the proximal perfusion port which is in fluid communication with the second inner lumen therein.

9. The balloon dilatation catheter of claim 8 wherein the multilumen distal section has a guidewire receiving port located in the distal end of the second inner lumen and in fluid communication therewith.

* * * * *